(12) United States Patent
Lim et al.

(10) Patent No.: US 12,025,995 B2
(45) Date of Patent: Jul. 2, 2024

(54) DRONE ASSISTING TRAINING OF ATHLETES AND OPERATING METHOD OF SAME

(71) Applicant: Joseph Lim, Gyeonggi-do (KR)

(72) Inventors: Joseph Lim, Gyeonggi-do (KR); Jae Whoon Cho, Gyeonggi-do (KR)

(73) Assignee: Joseph Lim, Gyeonggi-do (KR)

( * ) Notice: Subject to any disclaimer, the term of this patent is extended or adjusted under 35 U.S.C. 154(b) by 0 days.

(21) Appl. No.: 18/237,406

(22) Filed: Aug. 24, 2023

(65) Prior Publication Data

US 2024/0126274 A1   Apr. 18, 2024

(30) Foreign Application Priority Data

Oct. 13, 2022   (KR) .......................... 10-2022-0131173

(51) Int. Cl.
*G05D 1/00* (2024.01)
*A63B 71/06* (2006.01)

(52) U.S. Cl.
CPC ......... *G05D 1/106* (2019.05); *A63B 71/0622* (2013.01); *A63B 71/0686* (2013.01); *G05D 1/042* (2013.01); *A63B 2071/0625* (2013.01); *A63B 2220/806* (2013.01); *A63B 2220/808* (2013.01); *A63B 2230/00* (2013.01)

(58) Field of Classification Search
CPC .... G05D 1/106; G05D 1/042; A63B 71/0622; A63B 71/0686; A63B 2071/0625; A63B 2220/806; A63B 2220/808; A63B 2230/00
See application file for complete search history.

(56) References Cited

U.S. PATENT DOCUMENTS

| | | | |
|---|---|---|---|
| 11,048,277 B1* | 6/2021 | Zhu | G05D 1/12 |
| 11,740,630 B2* | 8/2023 | Bachrach | G06T 7/20 |
| | | | 701/3 |
| 2019/0377345 A1* | 12/2019 | Bachrach | G06V 20/13 |
| 2021/0258540 A1* | 8/2021 | Rajan Kesavelu Shekar | G10L 15/22 |
| 2022/0066478 A1* | 3/2022 | Kunwar | G05D 1/1062 |
| 2022/0108325 A1* | 4/2022 | Trunck | G06Q 10/083 |

FOREIGN PATENT DOCUMENTS

KR     10-1078020 B1    10/2011
KR  10-2015-0107451 A    9/2015

OTHER PUBLICATIONS

Jumpei Yamazaki, Examination of utilizing drone in guidance of athletics, Bulletin of Studies in Athletics of JAAF vol. 15, 98-105, 2019.
KIPO, Notification of Reason for Refusal, Korean Patent Application No. 10-2022-0131173, Mar. 20, 2023.
KIPO, Decision to Grant a Patent, Korean Patent Application No. 10-2022-0131173, Aug. 14, 2023.

\* cited by examiner

*Primary Examiner* — Masud Ahmed
(74) *Attorney, Agent, or Firm* — Nicholas Park

(57) ABSTRACT

A drone and an operating method for assisting player training are disclosed. The method for operating the drone for training sports events according to the technical idea of the present disclosure may include receiving a speed profile, starting acceleration based on a start signal, and controlling speed based on the speed profile, wherein the speed profile includes information on speed by time as a feature.

16 Claims, 11 Drawing Sheets

FIG. 5

|  | t1 | t2 | t3 | t4 | t5 | t6 | t7 | t8 |
|---|---|---|---|---|---|---|---|---|
| VP1 | tv11 | tv12 | tv13 | tv14 | tv15 | tv16 | tv17 | tv18 |
| VP2 | tv21 | tv22 | tv23 | tv24 | tv25 | tv26 | tv27 | tv28 |

FIG. 6

| | v1 | v2 | v3 | v4 | v5 | v6 |
|---|---|---|---|---|---|---|
| M1 | C11 | C12 | C13 | C14 | C15 | C16 |
| M2 | C21 | C22 | C23 | C24 | C25 | C26 |
| M3 | C31 | C32 | C33 | C34 | C35 | C36 |
| M4 | C41 | C42 | C43 | C44 | C45 | C46 |

T_mc

DRONE ASSISTING TRAINING OF ATHLETES AND OPERATING METHOD OF SAME

CROSS-REFERENCE TO RELATED APPLICATION

This application claims priority to Korean Patent Application No. 10-2022-0131173, filed on Oct. 13, 2022, and all the benefits accruing therefrom under 35 U.S.C. § 119, the contents of which are incorporated by reference in their entirety.

BACKGROUND

Technical Field

The present invention relates to a drone for assisting athlete training sport type and an operating method therefor.

Background Art

As national income increases, interest in sports continues to increase. There are various sports types including track and field events such as running, high jump, and long jump, weight training, and ball games such as soccer and badminton, and various videos and training tools are used for the training of professional athletes or ordinary people who want to improve their athletic abilities.

Among them, a pace maker may refer to a person who creates a standard velocity, or a person who helps reduce records by adjusting the pace of the athlete in record training or games of marathon, but it is difficult to find pace maker resources because there are few people with good records and physical conditions to serve as the pace maker.

SUMMARY

Technical Problem

An object of the present invention is to provide a drone for assisting training of an athlete and a method of operating the same.

Technical Solution

According to an embodiment of the present invention an operating method of a drone for training of athletes which includes a processor, the method comprises receiving, by the processor, a velocity profile including sport type information corresponding to any one of a plurality of sport type having different environments, starting, by the processor, acceleration based on a start signal and controlling, by the processor, velocity of the drone based on the velocity profile, wherein the velocity profile includes a plurality of average velocity information each corresponding to a time section of a record of a specific athlete, wherein the controlling of the velocity of the drone based on the velocity profile comprises, determining, by the processor, a motor operation table corresponding to the sport type information among a plurality of motor operation tables and operating, by the processor, a motor to correspond to the plurality of average velocity information for each time section using the determined motor operation table.

In an embodiment, wherein the starting of acceleration based on the start signal comprises, generating, by the processor, the start signal and starting, by the processor, acceleration of the drone in response to generation of the start signal.

In an embodiment, wherein the starting of acceleration based on the start signal comprises, recognizing, by the processor, the predetermined start signal and starting, by the processor, acceleration of the drone in response of recognition of the start signal.

In an embodiment, the operating method further comprising, recognizing, by the processor, a starting line for starting and adjusting, by the processor, a position of the drone to correspond to the starting line.

In an embodiment, wherein the starting of acceleration based on the start signal comprises, recognizing, by the processor, an athlete who becomes a subject of the training, adjusting, by the processor, a hovering height to correspond to a specific position of the athlete and starting, by the processor, acceleration based on the start signal at the adjusted hovering height.

In an embodiment, wherein the controlling of the velocity based on the velocity profile includes, recognizing, by the processor, a driving line, calculating, by the processor, a rotation angle based on the driving line and controlling, by the processor, the velocity including a direction corresponding to the rotation angle using the determined motor operation table.

In an embodiment, wherein the motor operation table is determined based on at least one of temperature, humidity and wind strength information of the sport type information.

According to an embodiment of the present invention, a drone used for training of athletes, the drone comprising, a motor configured to operate the drone, a memory configured to receive and store a velocity profile including a plurality of average velocity information each corresponding to a time section of a record of a specific athlete and a processor configured to control the motor based on the velocity profile, wherein the memory stores a motor operation table including information on control signals for operating the motor to correspond to the average velocity information, wherein the processor starts the drone by controlling the motor based on a start signal, further receives sport type information corresponding to any one of a plurality of sport types having different environments, determines a motor operation table corresponding to the sport type information among the plurality of motor operation tables stored in the memory, and operates the motor to correspond to the average velocity of the time section using the determined motor operation table.

In an embodiment, the drone further comprising, a speaker configured to generate the start signal, wherein the processor is configured to output the start signal using the speaker, and to transmit control signals for accelerating the drone in association with the start signal.

In an embodiment, the drone further comprising, a sound sensor configured to sense the start signal, wherein the processor is configured to transmit control signals for accelerating the drone in response of sensing the start signal by the sound sensor.

In an embodiment, the drone further comprising, a camera configured to sense a starting line for departure, wherein the processor is configured to adjust the position of the drone to correspond to the starting line by controlling the motor.

In an embodiment, the drone further comprising, a camera configured to recognize an athlete who becomes a subject of the training, wherein the processor is configured to adjust a hovering height of the drone to correspond to a specific position of the athlete by controlling the motor, and start acceleration based on the start signal at the adjusted hovering height.

In an embodiment, the drone further comprising, a camera configured to recognize a driving line, wherein the processor is configured to calculate a rotation angle based on the driving line and control a velocity of the drone including a direction of the drone to correspond to the rotation angle by using a determined motor operation table.

In an embodiment, wherein the motor operation table is determined based on at least one of temperature, humidity, and wind strength information of the sport type information.

Effects of the Invention

According to the technical idea of the present invention, a drone for controlling a velocity based on existing recording information is provided to help improve a record of a athlete, so that the athlete can adjust his or her pace according to the velocity of the drone, and thus the athlete can experience the improvement of the record without the help of others.

BRIEF DESCRIPTION OF THE DRAWINGS

FIG. 5 is a table showing velocity profiles according to an example embodiment.

FIG. 6 is a table showing a motor operation table according to an embodiment of the present invention.

DETAILED DESCRIPTION

Figure 1:
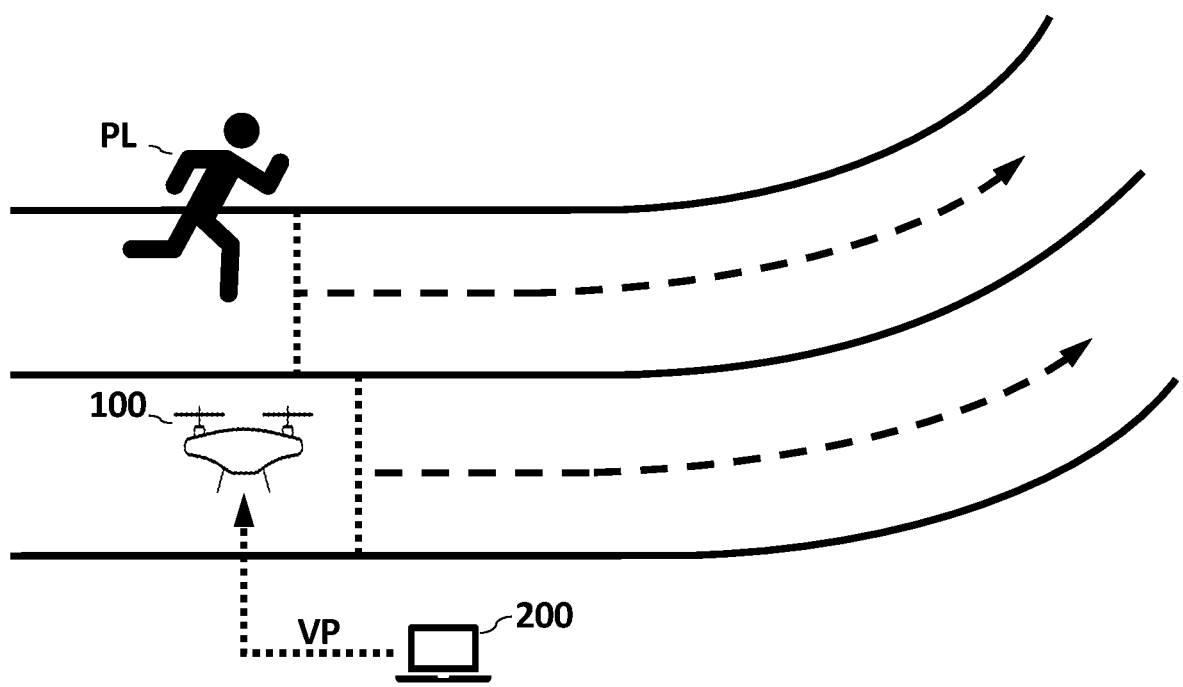
FIG. 1 is a diagram illustrating an operation of a drone operation system according to an embodiment of the present invention.

Hereinafter, exemplary embodiments of the present disclosure will be described in detail with reference to the accompanying drawings. Advantages and features of the present disclosure, and methods of achieving them will become apparent with reference to embodiments described in detail below together with the accompanying drawings. However, the technical spirit of the present disclosure is not limited to the following embodiments, but may be implemented in various different forms, and the following embodiments are provided to complete the technical spirit of the present disclosure and completely inform a person having ordinary skill in the art to which the present disclosure belongs of the scope of the present disclosure, and the technical spirit of the present disclosure is only defined by the scope of Claims.

In adding reference numerals to elements in each drawing, it should be noted that the same elements will be designated by the same reference numerals, if possible, although they are shown in different drawings. In addition, in describing the present disclosure, when it is determined that a detailed description of related known features or functions may obscure the gist of the present disclosure, the detailed description thereof will be omitted.

Unless otherwise defined, all terms (including technical and scientific terms) used herein have the same meaning as commonly understood by one of ordinary skill in the art to which the present disclosure belongs. In addition, terms defined in commonly used dictionaries are not interpreted ideally or excessively unless they are clearly specifically defined. The terminology used herein is for the purpose of describing embodiments and is not intended to limit the present disclosure. In the specification, a singular form includes a plural form unless specifically mentioned in the text.

In addition, in describing the feature element of the present disclosure, terms such as first, second, A, B, (a), (b), and the like may be used. The term is used only to distinguish the feature element from other feature elements, and the nature, sequence, or order of the corresponding feature element is not limited by the term. When a feature element is described as being "connected," "coupled," or "connected" to another element, the feature element may be directly connected or connected to the other element, but it should be understood that another feature element may be "connected," "coupled," or "connected" between each feature element.

"Comprises" and/or "comprising" used in the present disclosure does not exclude the presence or addition of one or more other feature elements, steps, operations and/or elements in the noted feature elements, steps, operations and/or elements.

A component included in any one embodiment and a feature element including a common function may be described using the same name in another embodiment. Unless otherwise stated, the description described in any one embodiment may be applied to other embodiments, and a detailed description may be omitted within a redundant range or a range that can be clearly understood by a skilled person in the art in the art.

Hereinafter, the present invention will be described in detail with reference to preferred embodiments of the present invention and the accompanying drawings.

FIG. 1 is a diagram illustrating an operation of a drone operation system according to an embodiment of the present invention.

Referring to FIG. 1, the drone operation system may include a drone 100 and a management terminal 200, and may serve to allow the athlete PL to adjust a pace while the drone 100 flies next to the athlete PL in order to improve records of the athlete PL. The drone 100 generally refers to a flight vehicle that flies unattended by inducing radio waves, and normally flies in the air by lift force of four propellers, but recently, drones using the number of various propellers such as six propellers and eight propellers have appeared. The drone 100 may be used in various environments and may be referred to as a multicopter, a drone, an unmanned aerial vehicle, or the like.

The management terminal 200 may transmit various control signals (e.g., a velocity profile VP and item information) for controlling the drone 100 to the drone 100. In one example, the management terminal 200 may be configured as any one of a laptop, a personal computer (PC), a personal communication system (PCS), a global system for mobile communications (GSM), a personal digital cellular (PDC), a personal handyphone system (PHS), a personal digital assistant (PDA), an international mobile telecommunication (IMT)-2000, a code division multiple access (CDMA)-2000, a W-code division multiple access (W-CDMA), a wireless broadband Internet (Wibro) terminal, a smart pad, a tablet PC, a cellular phone, and a smart phone. In the present specification, the management terminal 200 is illustrated as being implemented through a terminal, but this is only an embodiment, and each feature may be implemented through a communication hub such as a server.

The drone 100 may receive various types of information from the management terminal 200 and fly based on the received information. In an embodiment, the drone 100 may receive the velocity profile VP from the management terminal 200 and may include information on a velocity by time included in the received velocity profile VP, and the velocity by time may include information on a speed and a direction in which the drone 100 should fly for each time section after departure. In another embodiment, the velocity profile VP may include information on a velocity for each distance, and the velocity for each distance may include information on a speed and a direction in which the drone 100 should fly for each position away from the starting point. In an embodiment, the velocity profile VP may include information on a velocity by time or distance corresponding to a record of a specific athlete (e.g., an Olympic record, a World Record, etc.).

In an embodiment, the drone 100 may receive the sport type information from the management terminal 200 and determine various control signals for flight based on the sport type information. In one example, the drone 100 may change the motor operation table based on the sport type information, which will be described later in FIG. 6.

According to the technical idea of the present disclosure, the drone 100 may fly based on a velocity profile VP corresponding to a record of a specific athlete, and the athlete PL may train as if the specific athlete is running next to the athlete PL by training along the drone 100, and as a result, efficient training using the drone 100 may be possible without the specific athlete. In an example in which the sport type is running, the velocity profile VP may correspond to the world record of the Usain Bolt, and the athlete PL may experience a training effect as if he were running next to the Usain Bolt by running next to the drone 100 flying along the record of the Usain Bolt during the training process.

Figure 2:
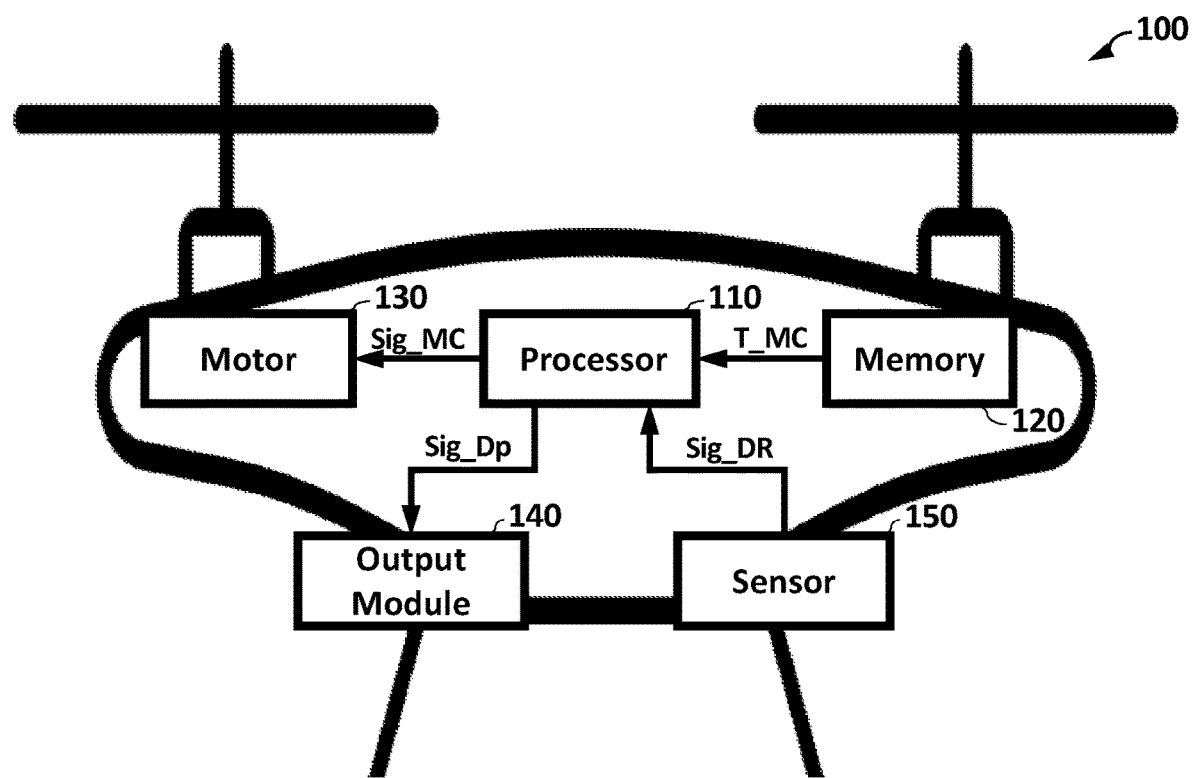
FIG. 2 is a diagram illustrating a drone according to an example embodiment.

FIG. 2 is a diagram illustrating a drone according to an example embodiment;

Referring to FIG. 2, the drone 100 may include a processor 110, a memory 120, a motor 130, an output module 140, and a sensor 150. The processor 110 may perform the operation of the drone 100 by controlling various features of the drone 100, and the operation performed by the drone 100 may be actually performed by the processor 110 using an application program embedded in the memory 120. The processor 110 may include at least one of a central processing unit (CPU), a graphic processing unit (GPU), a neural processing unit (NPU), a random access memory (RAM), a read only memory (ROM), a system bus, and an application processor.

The memory 120 may store various data for the operation of the drone 100, and in an example, the memory 120 may store a velocity profile VP and a motor operation table T_MC. The memory 120 may include a random access memory (RAM) and a storage, and in an example, may include a non-volatile memory, a volatile memory, a flash memory, a hard disk drive (HDD), a solid state drive (SSD), or the like.

The motor 130 may include a plurality of motors, and may perform upward movement, downward movement, forward movement, and rotational movement of the drone 100 by operating a propeller connected to the plurality of motors based on a motor control signal Sig_MC of the processor 110.

The output module 140 may include various output devices (e.g., a speaker, an LED, a bulb, a laser, an antenna, etc.) that output light, sound, and a signal, and may output a signal such as a sound, light, or the like that informs the athlete PL of a start based on a start signal Sig_Dp of the processor 110.

The sensor 150 may include various sensors (e.g., an ultrasonic sensor, an infrared sensor, a radar, a PSD sensor, an LiDAR, a ToF sensor, an image sensor, a stereo camera, a sound sensor, a microphone, etc.) for sensing light, sound, and a signal, and may sense a starting signal, a athlete, a starting line or a driving line in the playground, and output a sensing signal Sig_DR to the processor 110.

Although not illustrated, the drone 100 may include an acceleration sensor, a gyro sensor, and a geomagnetic sensor for flight, and may further include a communication module for communication with the management terminal 200.

In an embodiment, the processor 110 may receive the motor operation table T_MC from the memory 120 and control the motor 130 based on the motor control signal Sig_Dp obtained from the motor operation table T_MC by using the velocity profile VP received from the management terminal 200, thereby controlling the drone 100 to fly in response to the velocity profile VP.

In the present specification, the motor operation table may include information on a signal to be output for each of a plurality of motors in order to control the drone 100 at a desired velocity and direction.

In an embodiment, the processor 110 may recognize the starting line using the sensor 150 and control the motor 130 to correspond to the starting line, thereby controlling the drone 100 to automatically stand by at the starting line.

In an embodiment, the processor 110 may recognize a specific position of the athlete PL (for example, a chest position of the athlete) by using the sensor 150 and control the motor 130 to adjust the height of the drone 100 so that the user can hover at the specific position of the athlete PL.

In an embodiment, the processor 110 may recognize a start signal by using the sensor 150 and control the motor 130 in response to the start signal, thereby controlling the drone 100 to start simultaneously with the start signal.

In an embodiment, the processor 110 may recognize the driving line of the track of the playground using the sensor 150 and control the motor 130 so that the drone 100 moves along the driving line, thereby controlling the drone 100 to fly along the track even in the curved section.

According to an embodiment, the processor 110 may control the motor 130 to start the drone 100 at the same time as outputting the start signal to the athlete PL using the output module 140, thereby controlling to start the drone at the same time as the athlete PL.

According to various embodiments of the present disclosure, the drone 100 may fly according to the velocity profile VP simultaneously with the starting signal while waiting for departure to correspond to the athlete PL and the starting line, and continuously fly along the driving line, thereby giving a feeling that the athlete PL is running like a athlete having a record corresponding to the velocity profile VP, and accordingly, it may be very helpful for training the athlete PL.

Figure 3:
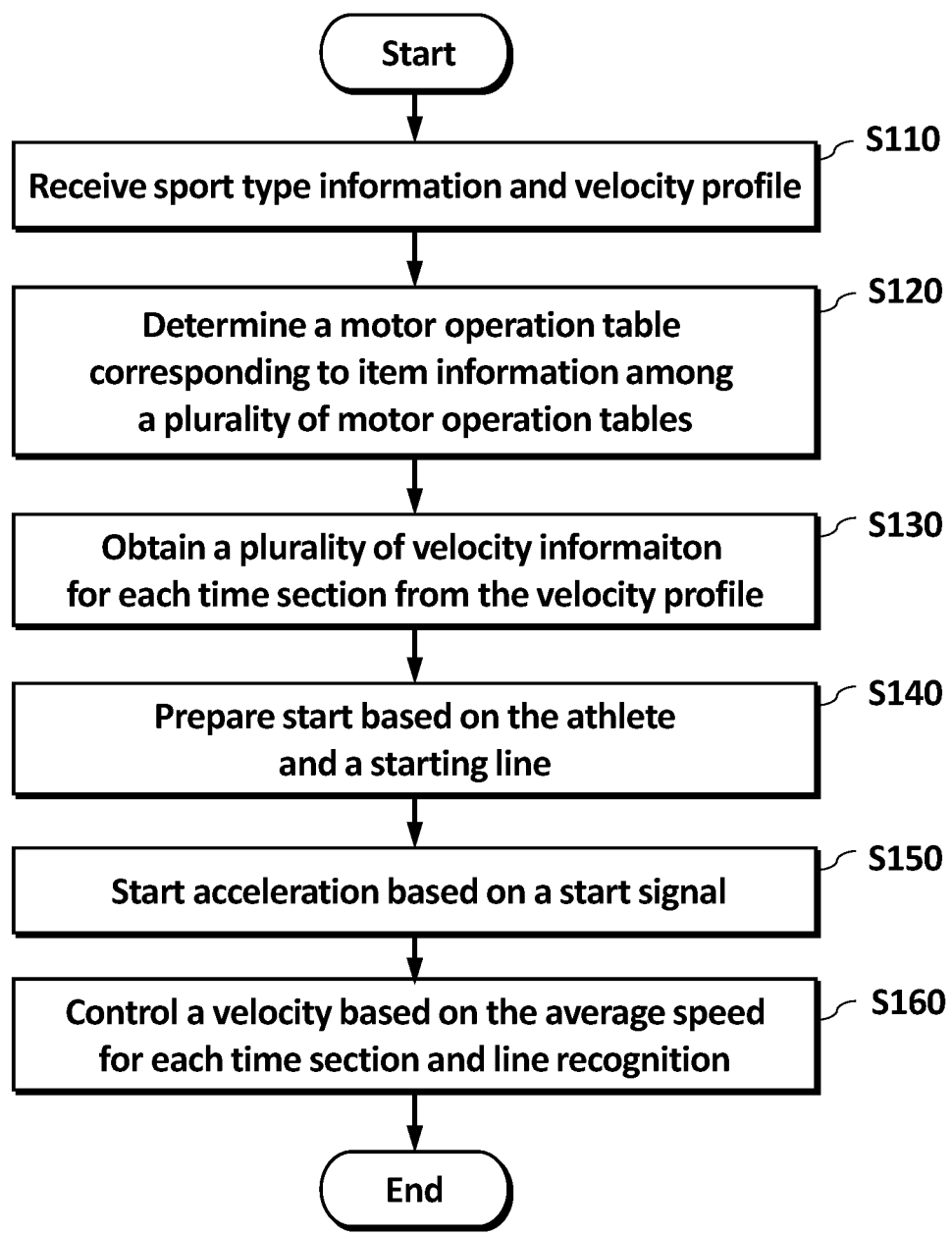
FIG. 3 is a flowchart illustrating a method of operating a drone according to an example embodiment.

FIG. 3 is a flowchart illustrating a method of operating a drone according to an example embodiment;

Referring to FIG. 3, the drone 100 may receive stock information and a velocity profile VP S110. The drone 100 may determine a motor operation table (T_MC) corresponding to the item information among a plurality of motor operation tables S120.

The control signal of the motor to be applied to achieve the desired velocity may be different for each event. For example, in the case of an indoor event such as an ice link, which is performed at a low temperature, since wind does not blow and air density is high, a desired velocity may be achieved at a different motion of the motor than an outdoor event such as a playground, which is performed at a high temperature. According to an embodiment of the disclosure, the drone 100 may achieve a desired velocity even in a plurality of events by differently setting a motor operation table for each type of sports and determining the motor operation table based on the received sport type information, and the drone 100 may be operated according to the velocity profile VP.

In another embodiment, the drone 100 may receive temperature and humidity and wind intensity information and determine a motor operation table T_MC corresponding to the temperature and humidity and wind intensity information.

The drone 100 may obtain a plurality of average velocity information for each time section from the velocity profile VP S130.

The drone 100 may prepare a departure based on the athlete and the departure line S140. In an embodiment, the drone 100 may recognize a specific position and a starting line of the athlete and perform hovering based thereon to prepare for departure, which will be described in detail with reference to FIG. 7.

The drone 100 may start acceleration based on the start signal S150. In an embodiment, the drone 100 may start acceleration simultaneously with generating the start signal, and in another embodiment, the drone 100 may start acceleration in response to the recognition of the start signal. This will be described in detail with reference to FIGS. 8 and 9.

The drone 100 may control the velocity based on the average velocity for each time section and line recognition S160. In an embodiment, the drone 100 may control the velocity based on the average velocity for each time section obtained from the velocity profile VP, and this will be described in detail with reference to FIGS. 4 to 6. In an embodiment, the drone 100 may control a direction by recognizing a driving line, and this will be described in detail in FIG. 10.

Figure 4:
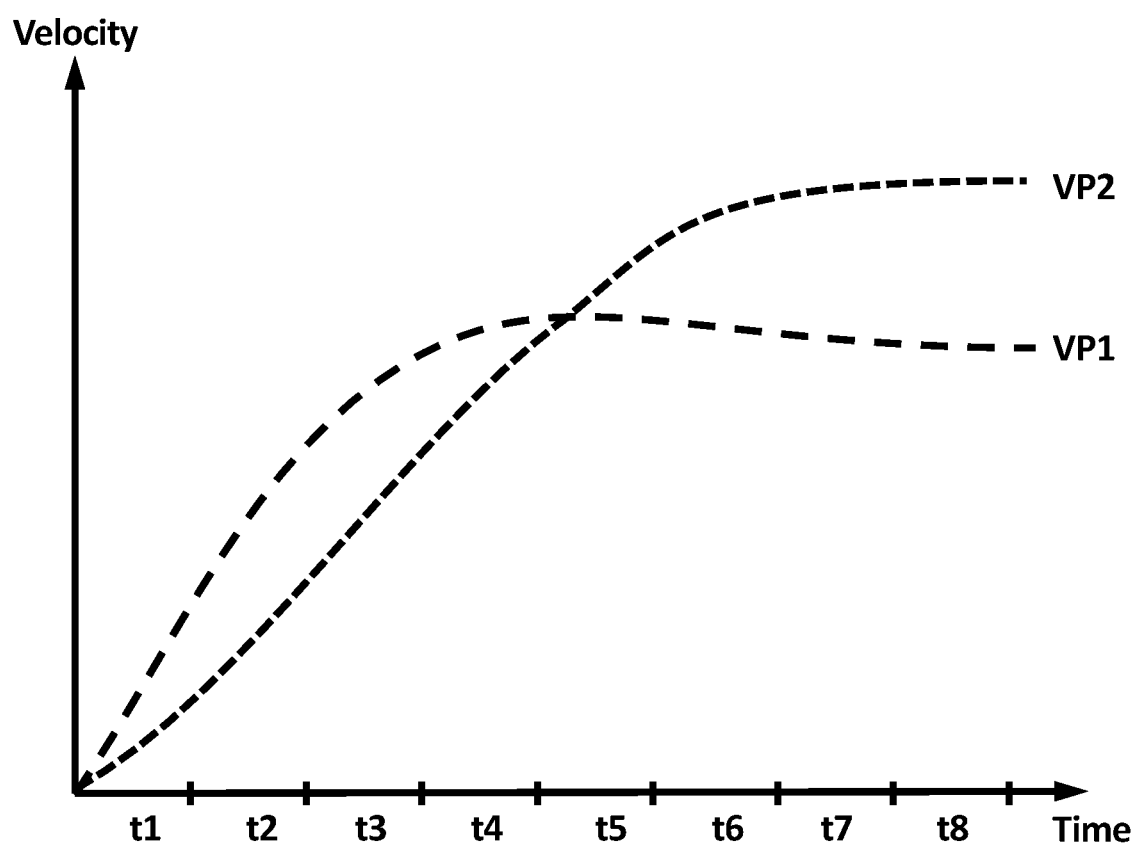
FIG. 4 is a diagram for describing a method of generating a velocity profile according to an example embodiment.

FIG. 4 is a diagram for describing a method of generating a velocity profile according to an example embodiment, and FIG. 5 is a table illustrating velocity profiles according to an example embodiment. In detail, FIG. 4 illustrates a graph corresponding to two different velocity profiles, in which an x-axis of the graph represents time and a y-axis represents velocity. Also, FIG. 5 illustrates a velocity profile including average velocity information for each time section so as to correspond to FIG. 4.

Referring to FIGS. 4 and 5, a time from a start to an end of a specific event is divided into N time sections t1 to t8, and a velocity profile may include the plurality of average velocity information that is the average velocity for each time section. In the example of FIG. 4, for convenience of description, an example in which the time period is divided into eight time periods is illustrated, but the time period may be divided into more or less than eight time periods.

The first velocity profile VP1 may include an average velocity tv11 to tv18 corresponding to each of the first time period t1 to the eighth time period t8, and the second velocity profile VP2 may include an average velocity tv21 to tv28 corresponding to each of the first time period t1 to the eighth time period t8. In one example, the average velocity tell to tv28 may be obtained by dividing the distance between the time sections by the unit time. In addition, in one example, the average velocity tv11 to tv28 may also include information on directions in addition to information on velocity.

In an example, a graph corresponding to the first velocity profile VP1 in the first time period t1 to the fourth time period t4 may have a higher average velocity than a graph corresponding to the second velocity profile VP2, and accordingly, an average velocity for each time period tv11 to tv14 included in the first velocity profile VP1 in the first time period t1 to the fourth time period t4 may be determined to be greater than the second velocity profile VP2. In an example, a graph corresponding to the second velocity profile VP2 in the fifth time period t5 to the eighth time period t8 may have a higher average velocity than a graph corresponding to the first velocity profile VP1, and accordingly, an average velocity tv25 to tv28 for each time period included in the second velocity profile VP2 in the first time period t1 to the fourth time period t4 may be determined to be greater than the first velocity profile VP1.

In an example, the first velocity profile VP1 may be a velocity profile corresponding to a record in which the initial spurt is good, and the second velocity profile VP2 may be a velocity profile corresponding to a record in which the highest velocity in the latter half is good. The athlete PL may train by inputting a velocity profile suitable for his or her training among a plurality of velocity profiles into the drone.

According to an embodiment of the disclosure, the velocity profiles VP1 and VP2 include information on the average velocity for each time period and the drone 100 operates based on the information, such that the drone 100 may implement different section velocity for each record that is the target of the velocity profile, and accordingly, the athlete PL who performs training may also be trained based on records suitable for training for the athlete PL.

FIG. 6 is a table showing a motor operation table according to an embodiment of the present invention.

Referring to FIG. 6, the motor 130 may include four motors M1 to M4, and the motor operation table T_mc may include information on the motor control signals C11 to C46 for each velocity v1 to v6. In an example, each of the velocity v1 to v6 may correspond to at least one of the average velocity tv11 to tv28 included in the velocity profiles VP1 and VP2.

In an example, the processor 110 may obtain a first velocity v1 as an average velocity corresponding to the first time period t1 of the velocity profile VP, and may obtain motor control signals C11 to C41 corresponding to the first velocity v1 based on the motor operation table T_mc. The processor 110 may output the first motor control signal C11 to the first motor M1, the second motor control signal C21 to the second motor M2, the third motor control signal C31 to the third motor M3, and the fourth motor control signal C41 to the fourth motor M4 in the first time period t1, thereby controlling the drone 100 to have the first velocity v1. In this way, the processor 110 may control the drone 100 to fly at a specific velocity using a motor control signal based on the velocity profile VP and the motor operation table T_mc for each time period.

The motor operation table T_mc may have different control signals by the sports type. So, the processor may determine a motor operation table corresponding to the sport type information among a plurality of motor operation tables and operate the motor to correspond to the plurality of average velocity information for each time section using the determined motor operation table. The control signal of the motor to be applied to achieve the desired velocity may be different for each sport type. According to an embodiment of the present invention, suitable control signal by the sport type may be applied to the motor based on the sport type information and the motor operation table, and the desired velocity of the drone may be achieved in spite of the various condition by the sport type.

Figure 7:
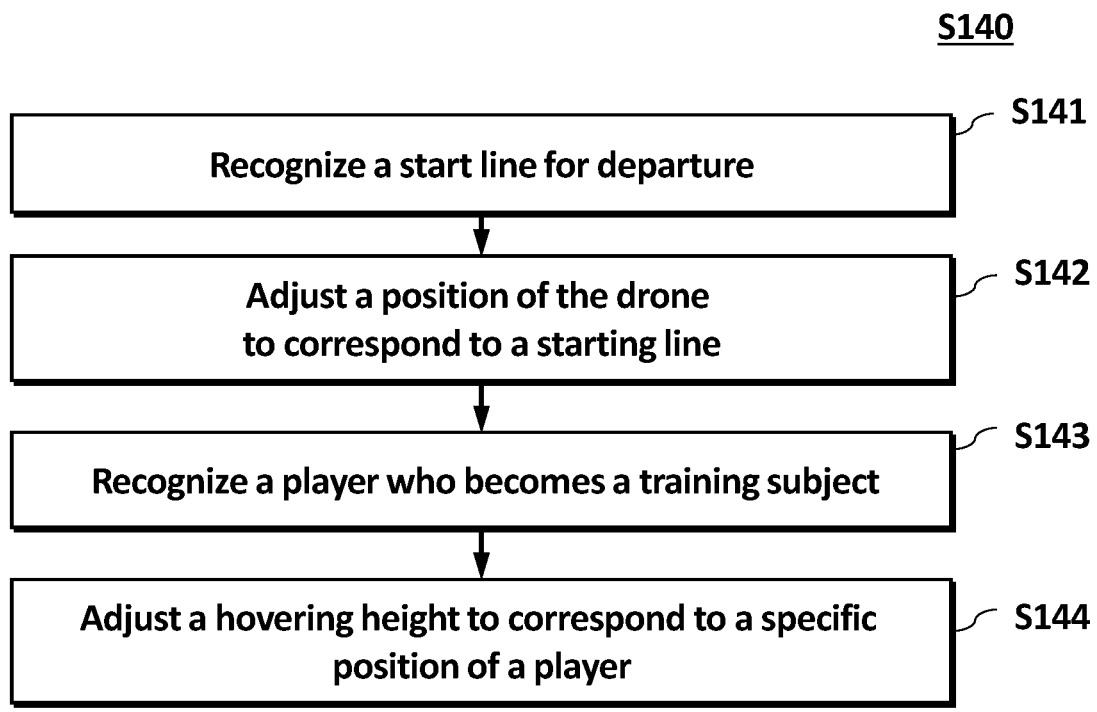
FIG. 7 is a flowchart illustrating a method for operating a drone according to an embodiment of the present invention.

FIG. 7 is a flowchart illustrating a method for operating a drone according to an embodiment of the present invention. In detail, FIG. 7 illustrates the start preparation (S140) of FIG. 3 in detail.

Referring to FIG. 7, the drone 100 may recognize a departure line S141. In an embodiment, the drone 100 may learn the starting line using a deep learning algorithm and recognize the starting line through an image sensor included in the sensor 150 using the learned artificial intelligence. The drone 100 may adjust the position of the drone 100 to correspond to the starting line S142. In an example, the processor 110 may control the motor 130 to adjust the position (e.g., x and y coordinates on the ground surface) of the drone 100 such that the drone 100 is positioned just behind the starting line.

The drone 100 may recognize an athlete PL who becomes a training subject S143. In an embodiment, the drone 100 may learn an athlete, which is a training target, by using a deep learning algorithm, and may recognize the athlete through an image sensor included in the sensor 150 by using the learned artificial intelligence. The drone 100 may adjust the hovering height to correspond to a specific position of the athlete S144. In an example, the processor 110 may control the motor 130 to adjust the height of the drone 100 (e.g., z coordinate on the ground surface) such that the drone 100 is positioned at the chest position of the athlete.

According to an exemplary embodiment of the present disclosure, the drone 100 automatically recognizes the starting line and the athlete PL and is automatically positioned at a standby position that is easily recognized by the athlete PL even right behind the starting line, so that the drone 100 can automatically wait for starting without separate control and the ease of control for the drone 100 can be increased.

Figure 8:
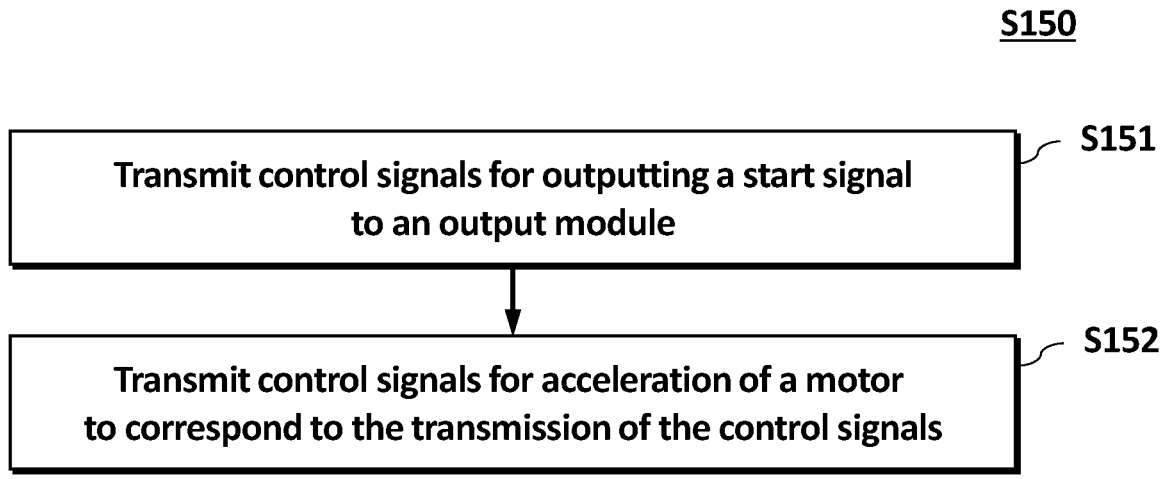
FIG. 8 is a flowchart of a method of operating a drone, according to an example embodiment.

FIG. 8 is a flowchart of a method of operating a drone, according to an example embodiment; In detail, FIG. 8 illustrates the acceleration start S150 of FIG. 3 in detail.

Referring to FIG. 8, the processor 110 may transmit a control signal Sig_Dp for outputting a start signal such as a sound or light to the output module 140 S151. Also, in response to the transmission of the control signal Sig_Dp, the processor 110 may transmit the control signal Sig_MC for the accelerated motion to the motor 130 S152. In an example, the processor 110 may transmit the control signal Sig_MC for the accelerated motion to the motor 130 simultaneously with the transmission of the control signal Sig_Dp. In this case, the control signal Sig_MC may be a control signal corresponding to a velocity profile. In another example, the processor 110 may transmit the control signal Sig_MC for the accelerated motion to the motor 130 after a predetermined time (e.g., an average starting signal reaction time of a athlete or a starting signal reaction time of a specific athlete) passes after the transmission of the control signal Sig_Dp.

Starting time in the record exercise is an important time to determine the rank, and the response velocity of athletes can be much faster than that of ordinary people. If the general public hears the start signal and controls acceleration of the drone 100, it may be impossible to reproduce an accurate record, considering that a reaction velocity of the general public is slower than that of the exercise athlete and a time for signal output and the drone 100 to receive and control the signal is added.

According to an embodiment of the disclosure, as the drone 100 directly outputs the start signal and performs the acceleration movement corresponding to the start signal, accurate recording may be reproduced as the drone 100 performs the acceleration movement in connection with the start signal, and in addition, as the athlete PL also performs training through the start signal, the utilization of training for the drone 100 may be significantly increased.

Figure 9:
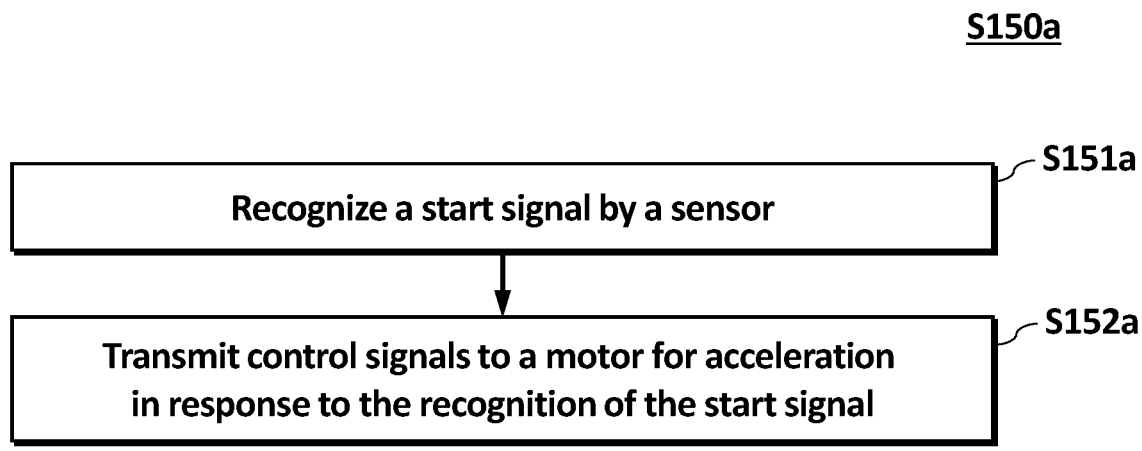
FIG. 9 is a flowchart illustrating a method for operating a drone according to an embodiment of the present invention.

FIG. 9 is a flowchart illustrating a method for operating a drone according to an embodiment of the present invention. In detail, FIG. 9 illustrates another embodiment of the acceleration start step S150a of FIG. 3 in detail.

Referring to FIG. 9, the processor 110 may recognize a start signal by the sensor 150 S151a. In an embodiment, the processor 110 may recognize a sound through the microphone of the sensor 150, and may determine whether the sound recognized through the microphone is a starting sound through deep learning. In another embodiment, when a sound recognized through the microphone of the sensor 150 corresponds to a specific frequency (for example, a frequency corresponding to a start signal), the processor 110 may recognize the sound as a start sound. A control signal Sig_MC for the accelerated motion may be transmitted to the motor 130 simultaneously with the recognition of the start signal S152a. In this case, the control signal Sig_MC may be a control signal corresponding to a velocity profile.

The athlete (PL) needs to perform training in an environment most similar to the actual environment for the game. According to an exemplary embodiment of the present disclosure, the drone 100 recognizes a start signal used in an actual game and performs an acceleration motion, so that the drone 100 may reproduce records associated with the start signal while the athlete PL trains using the start signal used in the actual game, and accordingly, the utilization of the drone 100 for training may be increased.

Figure 10:
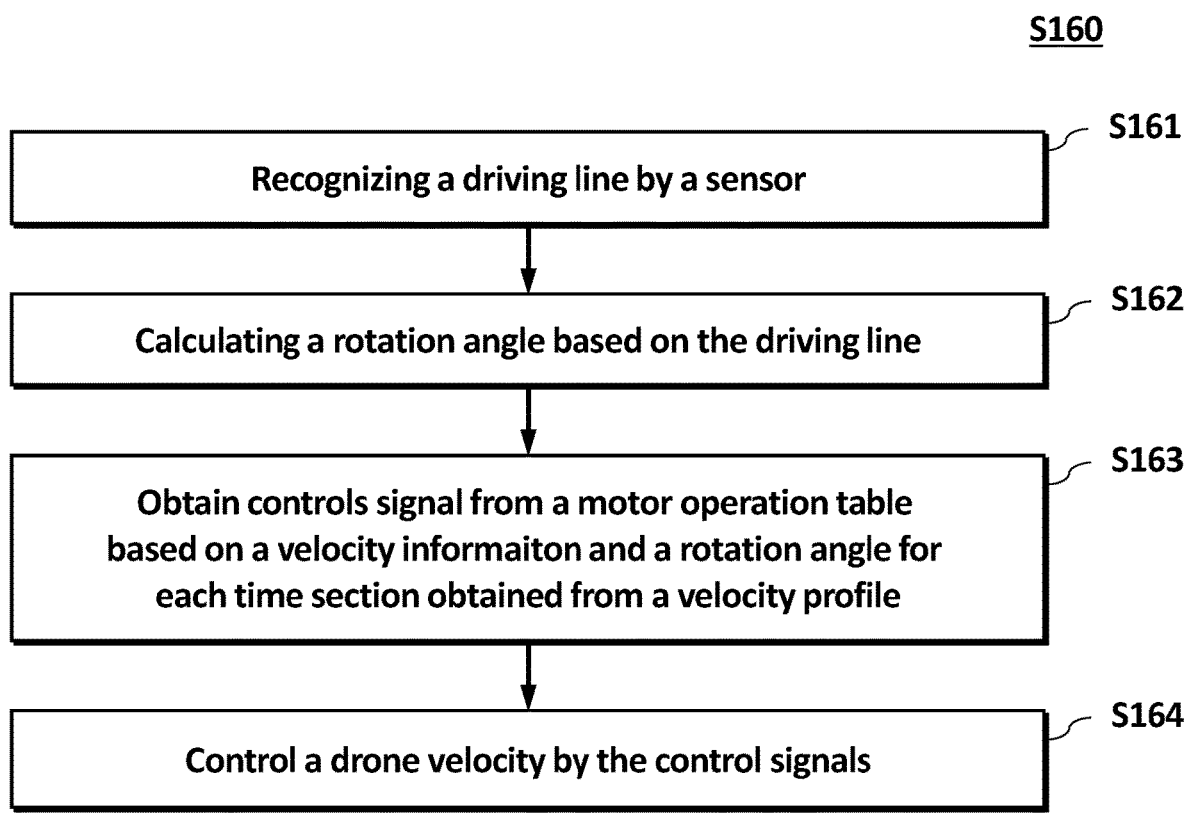
FIG. 10 is a flowchart of a method of operating a drone, according to an example embodiment.

FIG. 10 is a flowchart of a method of operating a drone, according to an example embodiment; In detail, FIG. 10 illustrates the velocity control method S160 of FIG. 3 in detail.

Referring to FIG. 10, when the sensor 150 recognizes a traveling line S161, the processor 110 may calculate a rotation angle based on the traveling line (S162). In one example, the camera included in the sensor 150 may photograph a traveling line, and the processor 110 may calculate an angle between a current traveling line and the traveling line bent in a curve.

The processor 110 may obtain a control signal from the motor operation table T_MC by reflecting the calculated rotation angle to the average velocity for each time period obtained from the velocity profile VP S163. In an example, the processor 110 may adaptively change the velocity to achieve the velocity obtained from the velocity profile VP even in the rotation period, and may obtain a motor control signal from the motor operation table T_MC to correspond to the changed velocity.

The processor 110 may control the velocity of the drone based on the obtained motor control signal S164.

Even if most exercise tracks are standardized, an error in the driving line may occur depending on the practice environment. According to an exemplary embodiment of the present disclosure, the velocity may be adaptively changed to achieve the same velocity as the recording in the changed track based on the driving line in spite of the change in the exercise track, and accordingly, training using the drone 100 in various environments may be possible.

Figure 11:
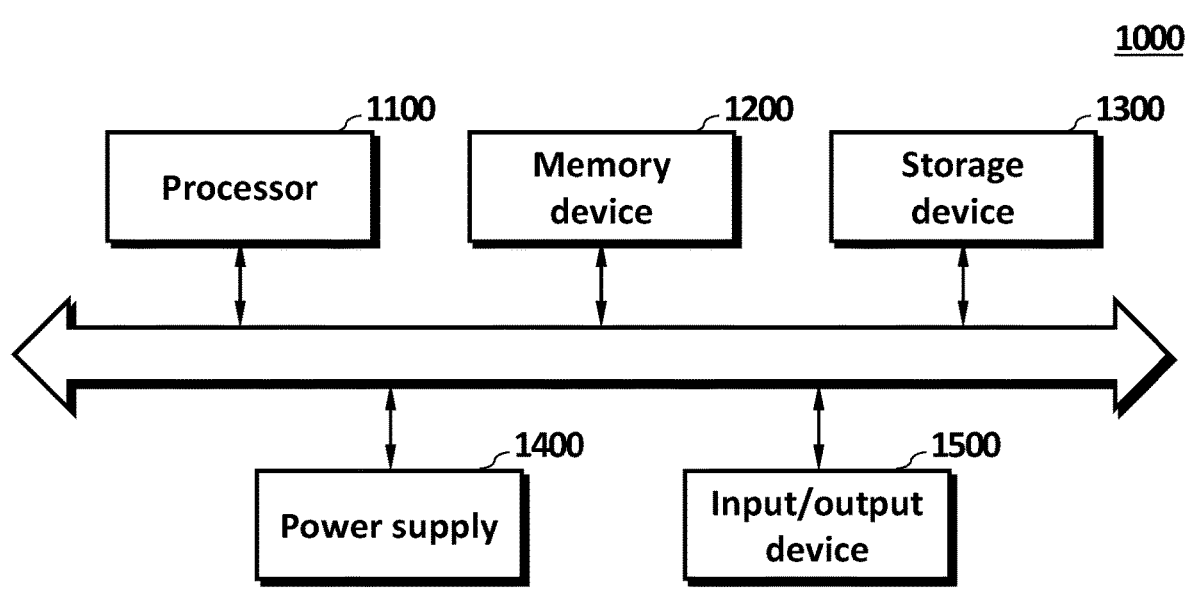
FIG. 11 is a block diagram illustrating a computing system including a management terminal according to an exemplary embodiment.

FIG. 11 is a block diagram illustrating a computing system including a management terminal according to an exemplary embodiment.

Referring to FIG. 11, a computing system 1000 may include a processor 1100, a memory device 1200, a storage device 1300, a power supply 1400, and an input/output device 1500. Although not illustrated in FIG. 11, the computing system 1000 may further include ports for communicating with a video card, a sound card, a memory card, a universal serial bus (USB) device, other electronic devices, etc.

As described above, the processor 1100, the memory device 1200, the storage device 1300, the power supply 1400, and the input/output device 1500 included in the computing system 1000 may constitute the management terminal 200 according to embodiments of the inventive concept. Specifically, the processor 1100 may perform the method of operating the drone described above with reference to FIGS. 1 to 10 through output of a control signal for the drone 110 by controlling the memory device 1200, the storage device 1300, the power supply 1400, and the input/output device 1500. Although a method of controlling the drone 100 itself is disclosed in FIGS. 1 to 10, the management terminal 200 may also implement the method of operating the drone of FIGS. 1 to 10 by controlling the drone 100 by configuring the computing system 1000.

The processor 1100 may perform various computing functions. The processor 1100 may be a microprocessor or a Central Processing Unit (CPU). The processor 1100 may communicate with the memory device 1200, the storage device 1300, and the input/output device 1500 through a bus 1600 such as an address bus, a control bus, or a data bus. According to an embodiment, the processor 1100 may be connected to an expansion bus such as a Peripheral Component Interconnect (PCI) bus.

The memory device 1200 may store data necessary for an operation of the computing system 1000. For example, the memory device 1200 may be implemented as a DRAM, a mobile DRAM, an SRAM, a PRAM, an FRAM, an RRAM, and/or an MRAM. The storage device 1300 may include a solid state drive, a hard disk drive, a CD-ROM, etc. The memory device 1200 and the storage device 1300 may store a program or data (e.g., a velocity profile, a motor operation table) related to the method of operating the drone described above with reference to FIGS. 1 to 10.

The input/output device 1500 may include an input device such as a keyboard, a keypad, a mouse, a microphone, an image sensor, etc., and an output device such as a printer, a display, a speaker, an LED, etc. The power supply 1400 may supply an operating voltage required for an operation of the computing system 1000.

In an embodiment, the processor 1100 may control the drone 100 to fly in response to the velocity profile VP using the velocity profile VP.

In an embodiment, the processor 1100 may control the drone 100 to automatically wait at the starting line.

In an embodiment, the processor 1100 may adjust the height of the drone 100 so that the drone 100 may hover at a specific position of the bow PL.

In an embodiment, the processor 1100 may recognize a start signal and control the drone 100 in response to the start signal, thereby controlling the drone 100 to start simultaneously with the start signal.

In an embodiment, the processor 110 may control the drone 100 to fly along the track even in the curved section.

In an embodiment, the processor 110 may control to start simultaneously with the athlete PL by starting the drone 100 at the same time as outputting the start signal to the athlete PL.

According to various embodiments of the present disclosure, the drone 100 may perform the above-described various operations by using the management terminal 200 as well as the drone 100 itself, and accordingly, it may be very helpful for training the athlete PL.

Exemplary embodiments have been disclosed in the drawings and in the specification as described above. Although embodiments have been described using specific terms in the present specification, they are used only for the purpose of describing the technical spirit of the present disclosure, and are not used to limit the meaning or limit the scope of the present disclosure described in Claims. Therefore, those skilled in the art will understand that various modifications and other equivalent embodiments are possible therefrom. Therefore, the true technical protection scope of the present disclosure should be determined by the technical idea of the appended claims.

What is claimed is:

1. An operating method of a drone for training of athletes which includes a processor, the method comprising:
   receiving, by the processor, sport type information corresponding to any one of a plurality of sport type having different environments, a velocity profile being stored in a memory of the drone, wherein the velocity profile includes a plurality of average velocity information, each average velocity information corresponding to a time section of a predetermined record of a specific athlete;
   transmitting, by the processor, acceleration signals to a motor of the drone based on a start signal;
   receiving, by the processor, at least one of temperature information, humidity information and wind strength information;
   determining, by the processor, a motor operation table corresponding to the sport type information and at least one of the temperature information, the humidity information and the wind strength information among a plurality of motor operation tables;
   transmitting, by the processor, velocity control signals to the motor of the drone, the velocity control signals corresponding to the plurality of average velocity information for each time section, based on the determined motor operation table;
   recognizing, by the processor, a driving line of a track using a camera of the drone;
   calculating, by the processor, a rotation angle based on difference between the driving line of the track and a moving line of the drone; and
   transmitting, by the processor, the velocity control signals to the motor of the drone to change a direction of the drone by the rotation angle, using the determined motor operation table, causing the drone to fly in the changed direction.

2. The operating method of the drone of claim 1, wherein the transmitting of the acceleration signals based on the start signal comprises:
generating, by the processor, the start signal; and
transmitting, by the processor, the acceleration signals to the motor of the drone in response to generation of the start signal.

3. The operating method of the drone of claim 1, wherein the transmitting of the acceleration signals based on the start signal comprises:
recognizing, by the processor, the start signal which is predetermined; and
transmitting, by the processor, the acceleration signals to the motor of the drone in response of recognition of the start signal.

4. The operating method of the drone of claim 1, further comprising:
recognizing, by the processor, a starting line for starting; and
adjusting, by the processor, a position of the drone to correspond to the starting line.

5. The operating method of the drone of claim 1, wherein the transmitting of the acceleration signals based on the start signal comprises:
recognizing, by the processor, an athlete who becomes a subject of the training;
adjusting, by the processor, a hovering height to correspond to a specific position of the athlete; and
transmitting, by the processor, the acceleration signals based on the start signal at the adjusted hovering height.

6. The operating method of the drone of claim 1, wherein the sport type information is received from a terminal.

7. The operating method of the drone of claim 1, wherein the plurality of sport type includes running.

8. The operating method of the drone of claim 1, wherein the flying drone serves as a pacemaker such that an athlete following the drone adjusts a pace based on the drone's movement.

9. The operating method of the drone of claim 1, wherein the predetermined record of the specific athlete comprises an official record including a world record, Olympic record, or a world record by the specific athlete.

10. A drone used for training of athletes, the drone comprising:
a motor configured to operate the drone;
a memory configured to receive and store a velocity profile including a plurality of average velocity information, each average velocity information corresponding to a time section of a predetermined record of a specific athlete;
a camera; and
a processor configured to control the motor based on the velocity profile,
wherein the memory stores a motor operation table including information on control signals for operating the motor to correspond to the average velocity information,
wherein the processor receives sport type information corresponding to any one of a plurality of sport type having different environments; transmits acceleration signals to the motor based on a start signal; senses at least one of temperature, humidity and wind strength to obtain at least one of temperature information, humidity information and wind strength information; determines a motor operation table corresponding to the sport type information and at least one of the temperature information, the humidity information and the wind strength information among a plurality of motor operation tables; transmits velocity control signals to the motor, the velocity control signals corresponding to the plurality of average velocity information for each time section, using based on the determined motor operation table; recognize a driving line of a track using the camera; calculates a rotation angle based on difference between the driving line of the track and a moving line of the drone; and transmits the velocity control signals to the motor to change a direction of the drone by the rotation angle, using the determined motor operation table such that the drone flies in the changed direction.

11. The drone of claim 10, further comprising:
a speaker configured to generate the start signal,
wherein the processor is configured to output the start signal using the speaker, and to transmit control signals for accelerating the drone in association with the start signal.

12. The drone of claim 10, further comprising:
a sound sensor configured to sense the start signal,
wherein the processor is configured to transmit control signals for accelerating the drone in response to sensing the start signal by the sound sensor.

13. The drone of claim 10,
wherein the camera is configured to sense a starting line for departure, and
wherein the processor is configured to adjust a position of the drone to correspond to the starting line by controlling the motor.

14. The drone of claim 10,
wherein the camera is configured to recognize an athlete who becomes a subject of the training, and
wherein the processor is configured to adjust a hovering height of the drone to correspond to a specific position of the athlete by controlling the motor, and start acceleration based on the start signal at the adjusted hovering height.

15. The drone of claim 10, wherein the motor includes a plurality of motors.

16. The drone of claim 15, wherein the plurality of motors are configured to perform upward movement, downward movement, forward movement, and rotational movement of the drone.

* * * * *